United States Patent [19]
Dekel

[11] Patent Number: 5,591,187
[45] Date of Patent: Jan. 7, 1997

[54] LAPAROSCOPIC TISSUE RETRIEVAL DEVICE AND METHOD

[76] Inventor: Moshe Dekel, 11 Ebbtide Ct., Oakdale, N.Y. 11769

[21] Appl. No.: 502,616

[22] Filed: Jul. 14, 1995

[51] Int. Cl.$^6$ ..................................................... A61B 17/14
[52] U.S. Cl. .......................................... 606/180; 606/170
[58] Field of Search ................................. 606/127, 178, 606/170, 180, 159, 128; 128/751, 755; 30/240, 133

[56] References Cited

U.S. PATENT DOCUMENTS

| | | |
|---|---|---|
| 696,902 | 4/1902 | Gary, Sr. . |
| 2,526,662 | 10/1950 | Hipps et al. . |
| 4,646,738 | 3/1987 | Trott . |
| 4,649,919 | 3/1987 | Thimsen et al. ......................... 128/305 |
| 5,195,954 | 3/1993 | Schnepp-Pesch et al. ............. 606/159 |
| 5,324,300 | 6/1994 | Elias et al. . |
| 5,376,100 | 12/1994 | Lefebure .................................. 606/180 |

Primary Examiner—Michael Powell Buiz
Assistant Examiner—Kevin Truong
Attorney, Agent, or Firm—Ostrolenk, Faber, Gerb & Soffen, LLP

[57] ABSTRACT

A material retrieval instrument, particularly for retrieving biological tissue. In one embodiment, the instrument comprises a cylindrical sheath having a distal end and a proximal end; an auger disposed in the sheath for rotation therein, the auger having a cutting blade disposed thereon, the cutting blade extending from the distal end of the sheath for engagement with tissue to be retrieved, the auger including a central longitudinal opening, the opening receiving an engaging member adapted to extend from the auger for engaging tissue to move the tissue into engagement with the cutting blade on the auger; the auger being rotatable in the sheath and comprising a conveyor for moving cut tissue longitudinally along the auger in the sheath to a tissue receiving reservoir; and a device for rotating the auger. In another embodiment, the instrument has an opening in a cylindrical surface of the sheath into which tissue to be excised can be fed for engagement with the cutting blade of the auger and subsequent removal.

64 Claims, 2 Drawing Sheets

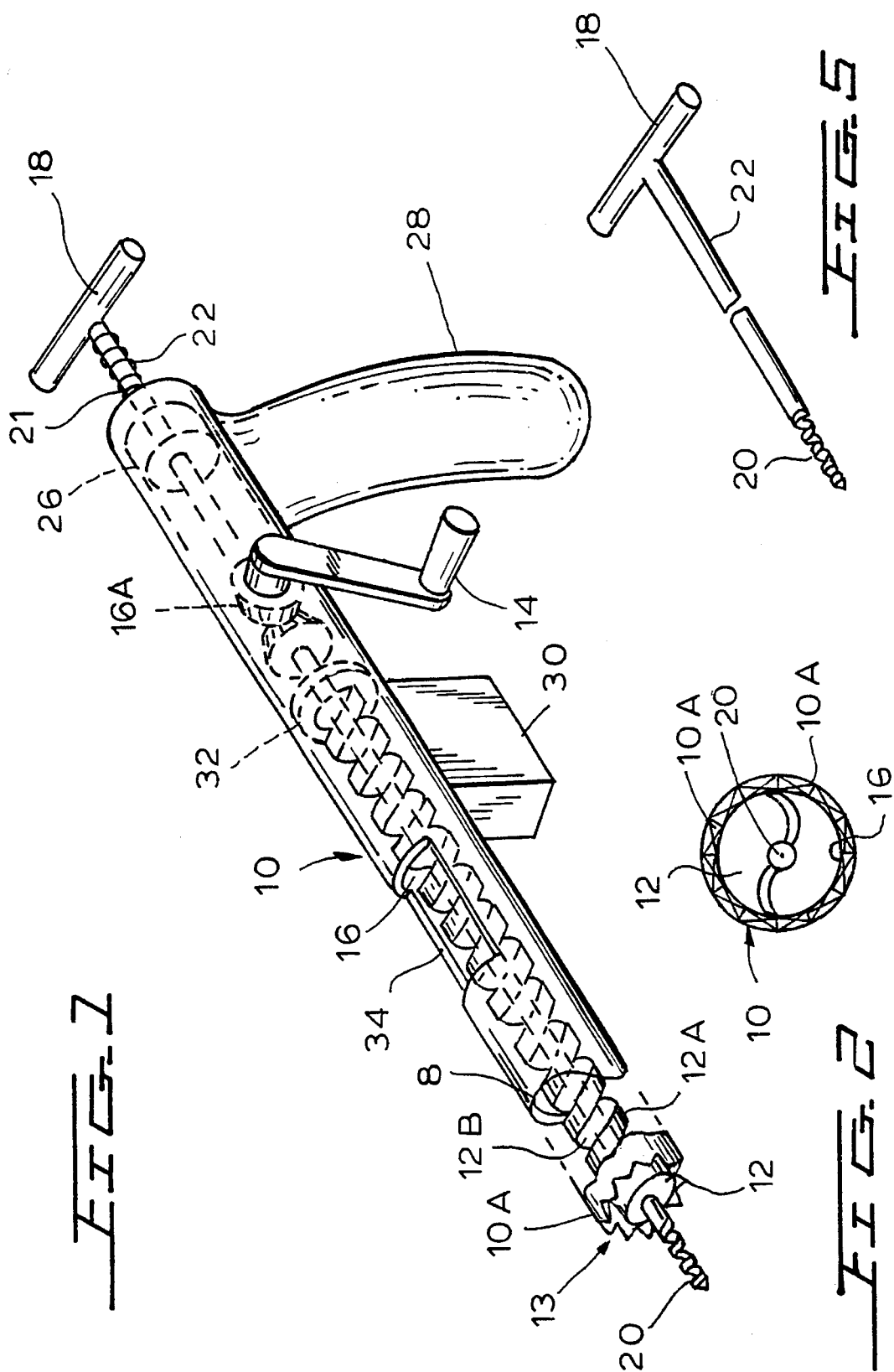

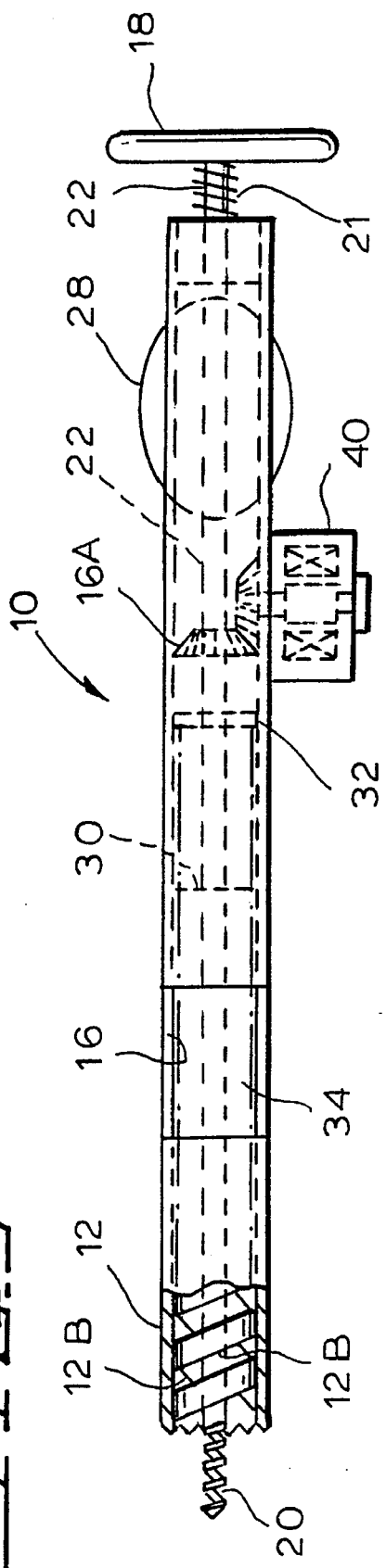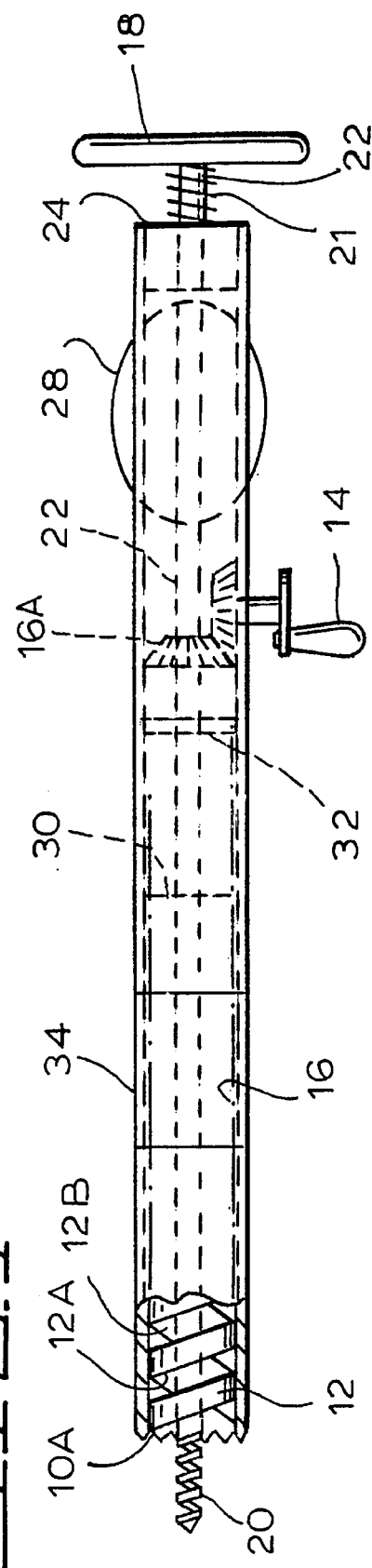

LAPAROSCOPIC TISSUE RETRIEVAL DEVICE AND METHOD

BACKGROUND OF THE INVENTION

The present invention relates to medical instruments and methods, and in particular, to laparoscopic medical instruments adapted to be inserted into the human body through minimally invasive surgical methods. The present invention relates, even more particularly, to a laparoscopic tissue retrieval device which can be inserted through minimally invasive surgical techniques into the human body to remove tissue, for example, myomas, tumors or other growths. In particular, the invention is adapted to remove tissue from within the peritoneal cavity during laparoscopic surgery.

Although the present invention is particularly suited for use as a surgical instrument, it may also find use as a device for retrieving materials other than biological tissues.

Applicant is aware of a number of references directed to surgical instruments for the removal of body tissue. These include Thimsen et al., U.S. Pat. No. 4,649,919; Elias et al., U.S. Pat. No. 5,324,300; Schnepp-Pesch et al., U.S. Pat. No. 5,195,954; Trott, U.S. Pat. No. 4,646,738; and Hipps et al , U.S. Pat. No. 2,526,662.

The Thimsen et al. reference discloses the use of an auger-like cutter blade which rotates within a stationary cylindrical sheath. The sheath is open at the distal end. The opening extends along the two sides of the sheath. The auger draws tissue approximately along the length of the cylindrical sheath. A vacuum hose provides suction necessary for the removal of severed tissue from a suction housing at the proximal end.

The Schnepp-Pesch et al. reference discloses an apparatus for the removal of deposits in vessels and organs. A helical attachment is pressed against a stone, for example, thus destroying it by rotation exerted by a shaft. Suction can take up deposits removed by the helical attachment and lead them into a hollow guidance tube.

The Trott reference discloses a rotary surgical tube wherein tissue is ground by a drill device and removed through a tube by suction.

The Elias et al. reference discloses a device for the controlled excision of a tissue sample or core from a living body. The device includes a means to prevent lateral movement of the cutting edge as it engages the tissue and a means to control the depth of excision. The device has an external sheath which is driven into the tissue with a coring shaft and which provides the operator with continued access to the sampling site after removal of the tissue core. In this device, the cutting shaft is a cylindrical member which rotates about a guide pin. The device is adapted to remove a core sample of biological tissue.

U.S. Pat. No. 2,526,662 to Hipps et al. discloses a bone meal extractor. This reference discusses the removal of bone meal through a small cutaneous incision. A drill is disposed within a tubular metal sleeve. As the drill grinds the bone, the bone meal is conveyed by the rotating drill to the interior of the sleeve where it is drawn down a tube into a cup for temporary storage.

Applicant is also aware of U.S. Pat. No. 6,696,902 to Gray for a boring tool, which discloses a drill bit disposed within a cylindrical sheath.

None of the references disclose or suggest a laparoscopic tissue retrieval device which provides the operator with a device that allows for the precision removal of tissue and a way to bring the tissue to be removed into precise alignment with the tissue cutting tool.

Further, none of the known devices provide a tissue retrieval device that can be used with out applying undue force on the tissue being removed or surrounding tissue. The known devices, therefore can damage the adjacent organs.

SUMMARY OF THE INVENTION

It is an object of the present invention to provide a device for the retrieval of material in general which cuts or grinds up the material and conveys the cut or ground-up material away from the site of the operation.

It is an object of the present invention to provide a medical instrument for the removal of biological tissue.

It is a further object of the present invention to provide such a medical instrument useful in the removal of biological tissue through minimally invasive laparoscopic techniques.

It is yet a further object of the present invention to provide a medical instrument which is useful in the removal of biological tissue from the peritoneal cavity or elsewhere in a human or animal body.

It is yet still a further object of the present invention to provide a laparoscopic tissue retrieval device which is adapted to immobilize tissue that is to be the subject of the removal operation, allow the tissue to be cut and conveyed away from the removal site to a reservoir.

It is yet still another object of the present invention to provide a laparoscopic tissue retrieval device which prevents rotation of the tissue to be removed as the tissue is selectively cut for removal.

It is yet still a further object of the present invention to provide a laparoscopic tissue retrieval device which allows the removal of tissue without applying forces to or damaging other adjacent body tissue, for example, other organs.

It is still yet a further object of the present invention to provide a laparoscopic tissue retrieval device which can be used with trocars used in laparoscopic minimally invasive surgical procedures.

It is yet still a further object of the present invention to provide a laparoscopic tissue retrieval device which is versatile in use, allowing the removal of both soft and hard tissue specimens.

It is yet still another object of the present invention to provide a laparoscopic tissue retrieval device which includes a window into which tissue to be removed can be inserted after severing from the organism and for conveying it to a tissue reservoir for removal.

It is yet still a further object of the present invention to provide a laparoscopic tissue retrieval device which can be employed for the removal of hard specimens, e.g., myomas, whereby the specimen is fixed in position without rotation while the device is employed to cut into the specimen to remove the hard tissue.

It is yet still a further object of the present invention to provide a laparoscopic tissue removal device which includes means to ensure continuous pneumo peritoneum, i.e., internal body pressure.

It is yet still another object of the present invention to provide methods for cutting or grinding up material, e.g., biological tissues, and for conveying the cut or ground-up material away from the operative site.

The above and other objects of the present invention are achieved by a material retrieval instrument comprising a cylindrical sheath having a distal open end and a proximal end; an auger disposed in the sheath for rotation therein, the auger having a cutting blade disposed thereon, the cutting blade extending from the distal open end of the sheath for engagement with material to be retrieved, the auger including a central longitudinal opening, the opening receiving an engaging member adapted to extend from the auger for engaging material to move the material into engagement with the cutting blade on the auger; the auger being rotatable in the sheath and comprising a conveyor for moving cut material longitudinally along the auger in the sheath to a material receiving reservoir; and a device for rotating the auger.

The objects of the invention are also achieved by a material retrieval instrument comprising a cylindrical sheath having a distal end and a proximal end; an auger disposed in the sheath for rotation therein, the auger having a cutting blade disposed thereon; the sheath having an opening in a cylindrical surface thereof into which material can be inserted for engagement with the cutting blade of the auger; the auger being rotatable in the sheath and comprising a conveyor for moving cut material longitudinally along the auger in the sheath to a material receiving reservoir; and a device for rotating the auger.

The objects of the invention are also achieved by a method for removal of material comprising:

rotating an auger having a cutting blade in a hollow cylindrical sheath, with the auger extending from a distal end of the sheath;

moving material to be removed into engagement with the rotating auger at the distal end;

conveying material cut by the auger along a longitudinal extent of the auger between the rotating auger and the sheath to a reservoir;

the step of moving material to be removed into engagement with the rotating auger comprising inserting an engaging device through a central opening in the auger so as to extend into engagement with the material to be removed, engaging the material and pulling it into contact with the rotating auger.

The objects of the invention are furthermore achieved by a method for removal of material comprising:

rotating an auger having a cutting blade in a hollow cylindrical sheath;

providing an opening in a cylindrical surface of the sheath, thereby exposing the cutting blade of the rotating auger;

moving material to be removed into engagement with the rotating auger through the opening; and conveying material cut by the auger along a longitudinal extent of the auger between the rotating auger and the sheath to a reservoir.

Other objects, features and advantages of the present invention will become apparent from the following detailed description of the invention.

BRIEF DESCRIPTION OF THE DRAWINGS

The above and other objects of the present invention will be apparent from the detailed description that follows taken in conjunction with the accompanying drawings in which:

FIG. 1 is a perspective partially cut-away and partially phantom view of the laparoscopic tissue retrieval device according to the present invention;

FIG. 2 is a front view of the laparoscopic tissue retrieval device showing the cutting blades housed within the cylindrical sheath;

FIG. 3 is a top plan view of the embodiment shown in FIG. 1;

FIG. 4 is a top plan view of a second embodiment wherein the cutting blades are driven by an electric motor; and FIG. 5 is a perspective view of an engaging tool forming a part of the invention.

DETAILED DESCRIPTION OF EMBODIMENTS OF THE INVENTION

With reference now to the drawings, FIG. 1 shows a perspective partial phantom, partial cut-away view of a first embodiment according to the present invention. Jagged line 8 reveals a cut-away portion of a part of the device, particularly the cutting device 12, to be discussed below. The laparoscopic tissue retrieval device comprises a cylindrical hollow sheath 10, preferably made of a clear plastic. The size of the sheath may be made such that it will be received within the interior of standard sized trocar devices, which are used to provide sheathed openings into a human or animal body during laparoscopic minimally invasive surgery. For example, the sheath 10 may be sized such that it fits within a 12 mm trocar or a 20 mm trocar, which are common trocar sizes. Of course, the invention is not limited to these particular diameters, and can be made of any size, as required, and also may be used without the use of trocar devices.

The sheath 10 has an internal bore which receives an auger or drill-like cutting device 12, which is disposed longitudinally and concentrically within the sheath 10 and which is adapted to be rotated by a suitable rotating device. In FIG. 1, the rotating device comprises a hand crank 14 as shown, driven through a gear arrangement 16, which may comprise two beveled gears, as shown more clearly in FIG. 3. The auger or drill-like rotatable cutting device 12 has a helical or spiral fluted cutting blade 12A disposed along its length. The cutting blade is sharpened at the distal end 13, where it comes into contact with tissue to be removed. It is also sharpened near a tissue insertion window 34, to be described below, and may also be serrated at this location.

The cutting device 12 functions both as a cutting blade and as a conveyor to move cut tissue along its length to a storage reservoir 30. Accordingly, it is preferable that the spiral cutting blade 12A be made as thin as possible, leaving a substantially large spiral conveying space 12B between adjacent edges of blade 12A for the conveyance of severed tissue material.

The cutting device 12 has a central longitudinal passageway 16 formed therein which is adapted to receive the shaft 22 of a T-handle device 18 having a corkscrew-like device 20 at the distal end thereof. The shaft 22 is received for slidable and rotatable movement within the passageway 16 and extends the entire length of the device, as shown in the drawings. Passageway 16 terminates at the distal end preferably in a cylindrical surface with sharpened edges to facilitate cutting. The cutting device 12 terminates at the gear drive 16, as shown more clearly in FIG. 3, with the shaft 22 of the T-handle device 18 extending past the proximal end of the cutting device 16 to the proximal end 24 of the sheath. Disposed at the proximal end 24 of the sheath is a pneumatic seal 26 in rotatable, sliding sealing engagement with the shaft 22 and which seals the interior of the sheath 10, and prevents, in the case of peritoneal surgery, e.g., pressure in the abdominal cavity from being released.

Also at the proximal end of the device, a hand grip 28 is provided so that the device can be conveniently handled by the surgeon.

About the midpoint of the sheath 10, a reservoir 30 is provided for receiving tissue conveyed by the rotating cutting device 12. Adjacent the reservoir, toward the proximal end of the device, a dam 32 is provided to prevent tissue from moving past the reservoir and for forcing the tissue conveyed by the cutting device 12 into the reservoir 30.

An opening 34 may also be provided in the sheath as shown. This opening is useful for providing tissue which can be manipulated into position adjacent the window to feed the tissue into the rotating cutting blade of the cutting device 12. The cutting device 12 has, as described, a sharp helical or spiral cutting blade, and in particular, adjacent the opening 34, the cutting blade may be serrated to facilitate maceration of the tissue.

FIG. 4 shows an alternative embodiment which employs an electric motor 40 to power the rotatable cutting device 12. In all other respects, the device is substantially the same as the device shown in FIGS. 1 and 3. Other power drive devices can also be used, e.g., pneumatic or hydraulic motors.

As described, the cutting device 12 has a central bore 16 provided therein through which the shaft 22 containing the corkscrew 20 is inserted. The purpose of the corkscrew 20 is to allow tissue to be engaged by a twisting action of the T-handle 18. Once the tissue is engaged, the corkscrew can be retracted by moving it longitudinally toward the operator, thereby to bring the tissue into engagement with the cutting teeth of the cutting device 12 disposed at the distal open end of the sheath 10. At the same time, the tissue engages with the serrated teeth 10A disposed along the distal cylindrical edge of the sheath 10. The purpose of the serrations 10A is to grip the tissue, thereby preventing the tissue from rotating as the rotating cutter 12 cuts into the tissue. The tissue is then removed by the conveying action of the rotating flutes of the device 12, which acts as a rotary conveyor to convey the tissue along the longitudinal length of the device, whereby it impacts against the dam 32, which causes the tissue then to be diverted into and received in the reservoir 30. The tissue can be removed by detaching or opening the reservoir 30, as desired.

According to a preferred embodiment of the invention, a coil spring 21 is provided encircling the proximal portion of the shaft 22 extending beyond sheath 10. The purpose of the spring 21 is to facilitate retraction of the tissue sample to be removed with out the need for an extra operative hand.

The sheath 10 is preferably made of a clear plastic, as described above, so that the tissue conveying action of the cutting device 12 can be visually observable. In addition, the device can be made both in reusable and disposable form. If reusable, it must be made so that it can be suitably disassembled and sterilized. Preferably, the device is made so that it is disposable, i.e., it is used only once and thereafter discarded.

As also discussed above, the pneumatic seal 26 is provided to maintain the internal body pressure, e.g., due to $CO_2$, of the peritoneal cavity or other body part, as is desirable. The pneumatic seal 26 may comprise a seal which closes when the shaft 22 containing corkscrew 20 and spring 21 is removed and which is in rotatable and slidable sealing engagement with the shaft 22 when the shaft 22 is inserted within the device.

As is evident from the drawings, the cutting device 12 can be rotated by manual means, as shown in FIG. 3, or by power means, as shown in FIG. 4, which shows an electric motor. As will be apparent to those of skill in the art, other devices can be employed to power the cutting device 12, for example, pneumatic or hydraulic actuating devices.

In operation, the device is used as follows:

For soft tissue specimens, the tissue removal preferably is accomplished utilizing the feeding window 34. The tissue is manipulated by other means into the area adjacent the window 34 and pushed into the window into engagement with the cutting blades. As discussed previously, the cutting blades near the window 34 may have serrations in order to macerate the tissue. The cut tissue is then propelled by the rotating auger device 12 against the dam 32 into the tissue reservoir 30. The procedure can be repeated until the tissue mass is removed.

If the tissue is a hard specimen, like a myoma, the corkscrew 20 is twisted via the T-handle 18 to engage the tissue sample. The corkscrew 20 is then retracted by pulling the handle 18 toward the operator or in the preferred embodiment, by the spring action of spring 21, which causes the specimen to be moved into engagement with the rotating auger 12 and the serrations 10A on the cylindrical sheath. The serrations 10A prevent the tissue sample from rotating as the auger cuts into the tissue. The pneumatic valve 26 assures continuous pneumo peritoneum. The procedure described can be repeated as needed to remove an entire specimen.

Other devices, such as a video camera attached to a laparoscope, fiber optic waveguides, and other instruments known to those of skill in the art, can be used to illuminate the surgical area and to provide a view of the surgical area, e.g., on a television monitor. This enables the surgeon to precisely position the device, engage the tissue with the corkscrew device 20 and provide the tissue into engagement with the cutting device 12. Similarly, these other devices also allow the tissue sample to be led to the window 34 for excision.

Although in the embodiments shown a tissue retrieval instrument is depicted having a sheath having both an open distal end through which the cutting device 12 extends and an opening 34 in the cylindrical surface of the sheath, the invention can be made without the opening 34, having only the open distal end 13 through which the cutting device 12 extends for cutting tissue. Alternatively, the device may not have the open distal end 13 and tissue to be excised is fed only into the opening 34 for removal.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A material retrieval instrument comprising:
  a cylindrical sheath having a distal open end and a proximal end;
  an auger disposed in the sheath for rotation therein, the auger having a cutting blade disposed thereon, the cutting blade extending from the distal open end of the sheath for engagement with material to be retrieved, the auger including a central longitudinal opening, the opening receiving an engaging member adapted to extend from the auger for engaging material to move the material into engagement with the cutting blade on the auger;

the auger being rotatable in the sheath and comprising a conveyor for moving cut material longitudinally along the auger in the sheath to a material receiving reservoir; and a device coupled to the auger for rotating the auger.

2. The material retrieval instrument of claim 1, wherein the engaging member comprises a corkscrew-like device extending from a shaft adapted for rotatable and slidable movement in the central longitudinal opening in the auger.

3. The material retrieval instrument of claim 2, further comprising a T-handle attached to the shaft.

4. The material retrieval instrument of claim 2, further comprising a pneumatic seal in sealing rotatable and slidable engagement with the shaft.

5. The material retrieval instrument of claim 2, further comprising a compression spring disposed about the shaft between the sheath and the proximal end of the shaft for providing a bias on the shaft toward the operator.

6. The material retrieval instrument of claim 1, wherein the device for rotating comprises a hand crank.

7. The material retrieval instrument of claim 1, wherein the device for rotating comprises an electric motor.

8. The material retrieval instrument of claim 1, wherein the device for rotating comprises a pneumatic or hydraulic drive.

9. The material retrieval instrument of claim 1, further comprising an opening in a cylindrical surface of the sheath through which material can be inserted for engagement with the cutting blade of the auger.

10. The material retrieval instrument of claim 9, wherein the cutting blade is serrated, at least in an area adjacent the opening in the sheath.

11. The material retrieval instrument of claim 1, further comprising a serrated edge at the distal end of the sheath for engaging material to be removed to prevent rotation of the material.

12. The material retrieval instrument of claim 1, further comprising a handle coupled to the sheath for grasping by a user.

13. The material retrieval instrument of claim 1, wherein the sheath is sized so as to fit within a trocar inserted in a body incision.

14. The material retrieval instrument of claim 13, wherein the sheath has an outer diameter of either approximately 12 mm or 20 mm.

15. The material retrieval instrument of claim 1, wherein the central opening in the auger is approximately 4 mm wide.

16. The material retrieval instrument of claim 1, wherein the sheath comprises a substantially transparent substance to enable visual observation of conveyance of material by the auger in the sheath.

17. The material retrieval instrument claim 16, wherein the sheath comprises a clear plastic.

18. The material retrieval instrument of claim 1, wherein the instrument is disposable.

19. The material retrieval instrument of claim 1, wherein the instrument is reusable.

20. The material retrieval instrument of claim 1, further comprising a dam adjacent the reservoir for directing cut material into the reservoir.

21. The material retrieval instrument of claim 1, wherein the material is biological tissue.

22. The material retrieval instrument of claim 1, wherein the auger has a helical cutting blade.

23. A material retrieval instrument comprising:

a cylindrical sheath having a distal end and a proximal end;

an auger disposed in the sheath for rotation therein, the auger having a cutting blade disposed thereon;

the sheath having an opening in a cylindrical surface thereof into which material can be inserted for engagement with the cutting blade of the auger;

the auger being rotatable in the sheath and comprising a conveyor for moving cut material longitudinally along the auger in the sheath to a material receiving reservoir; and a device coupled to the auger for rotating the auger.

24. The material retrieval instrument of claim 23, further wherein the distal end of the sheath is open and the cutting blade extends from the distal open end of the sheath for engagement with material to be retrieved.

25. The material retrieval instrument of claim 24, further wherein the auger includes a central longitudinal opening, the opening receiving an engaging member adapted to extend from the auger for engaging material to move the material into engagement with the cutting blade of the auger.

26. The material retrieval instrument of claim 25, further wherein the engaging member comprises a corkscrew-like device extending from a shaft adapted for rotatable and slidable movement in the central longitudinal opening in the auger.

27. The material retrieval instrument of claim 26, further comprising a T-handle attached to the shaft.

28. The material retrieval instrument of claim 26, further comprising a pneumatic seal in sealing rotatable and slidable engagement with the shaft.

29. The material retrieval instrument of claim 26, further comprising a compression spring disposed about the shaft between the sheath and the proximal end of the shaft for providing a bias on the shaft toward the operator.

30. The material retrieval instrument of claim 25, wherein the central opening in the auger is approximately 4 mm wide.

31. The material retrieval instrument of claim 24, further comprising a serrated edge at the distal end of the sheath for engaging material to prevent rotation of the material.

32. The material retrieval instrument of claim 23, wherein the device for rotating comprises a hand crank.

33. The material retrieval instrument of claim 23, wherein the device for rotating comprises an electric motor.

34. The material retrieval instrument of claim 23, wherein the device for rotating comprises a pneumatic or hydraulic drive.

35. The material retrieval instrument of claim 23, wherein the cutting blade is serrated, at least in an area adjacent the opening in the sheath.

36. The material retrieval instrument of claim 23, further comprising a handle coupled to the sheath for grasping by a user.

37. The material retrieval instrument of claim 23, wherein the sheath is sized so as to fit within a trocar inserted in a body incision.

38. The material retrieval instrument of claim 36, wherein the sheath has an outer diameter of either approximately 12 mm or 20 mm.

39. The material retrieval instrument of claim 23, wherein the sheath comprises a substantially transparent substance to enable visual observation of conveyance of material by the auger in the sheath.

40. The material retrieval instrument of claim 39, wherein the sheath comprises a clear plastic.

41. The material retrieval instrument of claim 23, wherein the instrument is disposable.

42. The material retrieval instrument of claim 23, wherein the instrument is reusable.

43. The material retrieval instrument of claim 23, further comprising a dam adjacent the reservoir for directing cut material into the reservoir.

44. The material retrieval instrument of claim 23, wherein the material is biological tissue.

45. The material retrieval instrument of claim 23, wherein the auger has a helical cutting blade.

46. A method for removal of material comprising:

rotating an auger having a cutting blade in a hollow cylindrical sheath, with the auger extending from a distal end of the sheath;

moving material to be removed into engagement with the rotating auger at the distal end so as to cut the material; and conveying material cut by the auger along a longitudinal extent of the auger between the rotating auger and the sheath to a reservoir;

the step of moving material to be removed into engagement with the rotating auger comprising inserting an engaging device through a central opening in the auger so as to extend into engagement with the material to be removed, engaging the material and pulling it into contact with the rotating auger.

47. The method of claim 46, further comprising contacting the material with the distal end of the sheath, with the distal end of the sheath engaging the material to prevent rotation of the material when the auger cuts into the material.

48. The method of claim 46, further comprising maintaining a pressurized atmosphere within the sheath.

49. The method of claim 46, further comprising manually rotating the auger.

50. The method of claim 46, further comprising rotating the auger using an electric drive motor.

51. The method of claim 46, further comprising rotating the auger using a pneumatic or hydraulic drive.

52. The method of claim 46, wherein the step of moving material to be removed into engagement with the auger comprises inserting a corkscrew engaging device into contact with the material to be removed, twisting the corkscrew into the material and retracting the corkscrew to bring the material into engagement with the auger.

53. The method of claim 46, further comprising providing an opening in a cylindrical surface of the sheath, moving material to be removed into engagement with the rotating auger exposed through the window, thereby cutting the material, and conveying the cut material along the auger in the sheath to the reservoir.

54. The method of claim 46 wherein the material comprises biological tissue.

55. A method for removal of material comprising:

rotating an auger having a cutting blade in a hollow cylindrical sheath;

providing an opening in a cylindrical surface of the sheath, thereby exposing the cutting blade of the rotating auger;

moving material to be removed into engagement with the rotating auger through the opening so as to cut the material; and conveying tissue cut by the auger along a longitudinal extent of the auger between the rotating auger and the sheath to a reservoir.

56. The method of claim 55, further comprising maintaining a pressurized atmosphere within the sheath.

57. The method of claim 55, further comprising manually rotating the auger.

58. The method of claim 55, further comprising rotating the auger using an electric drive motor.

59. The method of claim 55, further comprising rotating the auger using a pneumatic or hydraulic drive.

60. The method of claim 55, further comprising providing the sheath with an open distal end with the auger extending from the open distal end; and moving material to be removed into engagement with the rotating auger at the distal end of the sheath to cut the material.

61. The method of claim 60, wherein the step of moving material to be removed into engagement with the rotating auger at the distal end comprises inserting an engaging device through a central opening in the auger so as to extend into engagement with the material to be removed, engaging the material and pulling it into contact with the rotating auger.

62. The method of claim 61, further comprising contacting the material with the distal end of the sheath, with the distal end of the sheath engaging the material to prevent rotation of the material when the auger cuts into the material.

63. The method of claim 61, wherein the step of moving material to be removed into engagement with the auger comprises inserting a corkscrew engaging device into contact with the material to be removed, twisting the corkscrew into the material and retracting the corkscrew to bring the material into engagement with the auger.

64. The method of claim 55, wherein the material comprises biological tissue.

* * * * *